United States Patent [19]

McCall

[11] Patent Number: 4,927,563
[45] Date of Patent: May 22, 1990

[54] ANTIDANDRUFF SHAMPOO COMPOSITIONS CONTAINING A MAGNESIUM ALUMINUM SILICATE-XANTHAN GUM SUSPENSION SYSTEM

[75] Inventor: Patrick C. McCall, Cincinnati, Ohio

[73] Assignee: Procter & Gamble Company, Cincinnati, Ohio

[21] Appl. No.: 148,728

[22] Filed: Jan. 26, 1988

[51] Int. Cl.$^5$ .............................................. A61K 7/075
[52] U.S. Cl. ................................. 252/551; 252/174.15; 252/174.17; 252/174.25; 252/544; 252/549; 252/550; 252/DIG. 5; 252/DIG. 13; 424/70; 424/DIG. 4
[58] Field of Search .......... 252/549, DIG. 13, 174.15, 252/174.25, 312, 174.17, 544, DIG. 5, 550, 551; 424/70

[56] References Cited

U.S. PATENT DOCUMENTS

| | | | |
|---|---|---|---|
| 4,089,945 | 5/1978 | Brinkman et al. | 424/164 |
| 4,364,837 | 12/1982 | Pader | 252/173 |
| 4,470,982 | 9/1984 | Winkler | 252/DIG. 13 |
| 4,603,046 | 7/1986 | Georgalas et al. | 424/60 |
| 4,728,457 | 3/1988 | Fieler et al. | 252/174.15 |
| 4,803,774 | 5/1989 | LaPetina | 252/174.24 |

FOREIGN PATENT DOCUMENTS 1051268 12/1966 United Kingdom .

*Primary Examiner*—A. Lionel Clingman
*Assistant Examiner*—A. Beadles-Hay
*Attorney, Agent, or Firm*—Douglas C. Mohl; Steven J. Goldstein; Leonard Williamson

[57] ABSTRACT

Disclosed are selenium sulfide lotion shampoos containing a mixture of xanthan gum and magnesium aluminum silicate as a suspending system.

7 Claims, No Drawings

ANTIDANDRUFF SHAMPOO COMPOSITIONS CONTAINING A MAGNESIUM ALUMINUM SILICATE-XANTHAN GUM SUSPENSION SYSTEM

TECHNICAL FIELD

The present invention is related to lotion antidandruff shampoos containing selenium sulfide, which shampoos achieve improved deposition of the selenium sulfide particles through the use of a combination of xanthan gum and magnesium aluminum silicate as a suspension system.

BACKGROUND OF THE INVENTION

Lotion shampoos are widely accepted due to their ease of use, including spreading the shampoo through the hair. However, when particulate, small size active ingredients are used in lotion shampoos, suspension and deposition of those ingredients such as selenium sulfide presents a variety of problems.

The prior art discloses antidandruff shampoos containing components designed to suspend particulate matter. Japanese Application with Open for Public Inspection No. 60,810, May 19, 1977 (Lion Fat & Oil), dicloses shampoos containing 5% to 50% of an anionic surfactant, 1% to 10% of a fatty acid diethanol amide, 0.1% to 10% of an insoluble fine powder and 1% to 10% of an ethylene glycol ester. U.S. Pat. No. 4,470,982, to Winkler discloses similar compositions containing from 11% to 20% of an anionic surfactant, from 4% to 6% of a suspending agent, from 2% to 4% of an amide, a particulate antidandruff agent and water. British Patent 1,051,258, Dec. 14, 1966 to Colgate-Palmolive Company discloses selenium sulfide shampoos containing suspending agents.

While these references disclose suspending antidandruff actives, they do not provide all of the answers to the problems associated with forming such suspensions.

It has been surprisingly found by the present inventor that selenium sulfide lotion shampoo compositions utilizing xanthan gum and magnesium aluminum silicate as suspending agents are very stable and provide enhanced deposition of the selenium sulfide active.

It is an object of the present invention, therefore, to provide stable selenium sulfide lotion shampoos.

It is a further object of the present invention to provide selenium sulfide lotion shampoos utilizing a combination of xanthan gum and magnesium aluminum silicate suspending agents.

It is a still further object of the present invention to provide methods of shampooing hair with improved selenium sulfide compositions.

These and other objects will become readily apparent from the detailed description which follows.

Unless otherwise indicated, all percentages and ratios herein are by weight. Additionally, all measurements are made at 25° C. in the composition or on the pure material unless otherwise specified.

SUMMARY OF THE INVENTION

The present invention relates to lotion shampoo compositions comprising from about 10% to about 30% of a synthetic surfactant, from about 0.1% to about 5.0% of particulate selenium sulfide having an average particle size of less than 25 μm, from about 0.05% to about 1.0% of a xanthan gum, from about 0.10% to about 3.00% of a magnesium aluminum silicate, and water. These as well as optional components are described in detail below.

DETAILED DESCRIPTION

The essential components of the present invention as well as optional components are given in the following paragraphs.

Surfactant

An essential component of the present compositions is a surfactant. The surfactant, which may be selected from any of a wide variety of synthetic anionic, amphoteric, zwitterionic and nonionic surfactants, is present at a level of from about 10% to about 30%, preferably from about 15% to about 22%, most preferably from about 18% to about 20%.

Synthetic anionic surfactants can be exemplified by the alkali metal salts of organic sulfuric reaction products having in their molecular structure an alkyl radical containing from 8-22 carbon atoms and a sulfonic acid or sulfuric acid ester radical (included in the term alkyl is the alkyl portion of higher acyl radicals). Preferred are the sodium, ammonium, potassium or triethanolamine alkyl sulfates, especially those obtained by sulfating the higher alcohols ($C_8$-$C_{18}$ carbon atoms), sodium coconut oil fatty acid monoglyceride sulfates and sulfonates; sodium or potassium salts of sulfuric acid esters of the reaction product of 1 mole of a higher fatty alcohol (e.g., tallow or coconut oil alcohols) and 1 to 12 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; water soluble salts of condensation products of fatty acids with sarcosine; and other known in the art.

Zwitterionic surfactants can be exemplified by those which can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

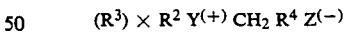

wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; $R^3$ is an alkyl or monohydroxyalkyl group containing 1 to about 3 carbon atoms; X is 1 when Y is a sulfur atom and 2 when Y is a nitrogen or phosphorus atom; $R^4$ is an alkylene or hydroxyalkylene of from 1 to about 4 carbon atoms and Z is a radical selected from the group consisting of carboxylate, sulfonate, sulfate, phosphonate, and phosphate groups.

Examples include:
4-[N,N-di(2-hydroxyethyl)-N-octadencylammonio]-butane-1-carboxylate;
5-[S-3-hydroxypropyl-S-hexadecylsulfonio]-3-hydroxypentane-1-sulfate;

3-[P,P-diethyl-P-3,6,9-trioxatetradexocylphosphonio]-2-hydroxypropane-1-phosphate;

3-[N,N-dipropyl-N-3-dodecoxy-2-hydroxypropylammoniol-propane-1-phosphonate;

3-(N,N-dimethyl-N-hexadecylammonio)propane-1-sulfonate;

3-(N,N-dimethyl-N-hexadecylammonio)-2-hydroxypropane-1-sulfonate;

4-[N,N-di(2-hydroxyethyl)-N-(2-hydroxydodecyl)ammonio]-butane-1-carboxylate;

3-[S-ethyl-S-(3-dodecoxy-2-hydroxypropyl)sulfonio]-propane-1-phosphate;

3-[P,P-dimethyl-P-dodecylphosphonio]-propane-1-phosphonate; and

5-[N,N-di(3-hydroxypropyl)-N-hexadecylammonio]-2-hydroxypentane-1-sulfate.

Other zwitterionics such as betaines are also useful in the present invention. Examples of betaines useful herein include the high alkyl betaines such as coco dimethyl carboxymethyl betaine, lauryl dimethyl carboxymethyl betaine, lauryl dimethyl alpha-carboxyethyl betaine, cetyl dimethyl carboxymethyl betaine, lauryl bis-(2-hydroxy-ethyl) carboxy methyl betaine, stearyl bis-(2-hydroxy-propyl) carboxymethyl betaine, oleyl dimethyl gamma-carboxypropyl betaine, lauryl bis-(2-hydroxypropyl) alpha-carboxyethyl betaine, etc. The sulfobetaines may be represented by coco dimethyl sulfopropyl betaine, stearyl dimethyl sulfopropyl betaine, lauryl dimethyl sulfoethyl betaine, lauryl bis-(2-hydroxy-ethyl) sulfopropyl betaine and the like; amido betaines and amidosulfobetaines, wherein the RCONH(CH$_2$)$_3$ radical is attached to the nitrogen atom of the betaine are also useful in this invention.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528,378.

Nonionic surfactants, which are preferably used in combination with an anionic, amphoteric or zwitterionic surfactant, can be broadly defined as compounds produced by the condensation of alkylene oxide groups (hydrophilic in nature) with an organic hydrophobic compound, which may be aliphatic or alkyl aromatic in nature, Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration, with ethylene oxide, e.g., a coconut alcohol ethylene oxide condensate having from 10 to 30 moles of ethylene oxide per mole of coconut alcohol, the coconut alcohol fraction having from 10 to 14 carbon atoms.

4. Long chain tertiary amine oxides corresponding to the following general formula:

wherein R$_1$ contains an alkyl, alkenyl or monohydroxy alkyl radical of from about 8 to about 18 carbon atoms, from 0 to about 10 ethylene oxide moieties, and from 0 to 1 glyceryl moiety, and R$_2$ and R$_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyldodecylamine oxide, oleyldi(2-hydroxyethyl) amine oxide, dimethyloctylamine oxide, dimethyl-decylamine oxide, dimethyltetradecylamine oxide, 3,6,9-trioxaheptadecyldiethylamine oxide, di(2-hydroxyethyl)-tetradecylamine oxide, 2-dode-coxyethyldimethylamine oxide, 3-dodecoxy-2-hydroxypropyldi(3-hydroxypropyl)amine oxide, dimethylhexadecylamine oxide.

5. Long chain tertiary phosphine oxides corresponding to the following general formula:

wherein R contains an alkyl, alkenyl or monohydroxyalkyl radical ranging from 8 to 18 carbon atoms in chain length, from 0 to about 10 ethylene oxide moieties and from 0 to 1 glyceryl moiety and R' and RΔ are each alkyl or monohydroxyalkyl groups containing from 1 to 3 carbon atoms. The arrow in the formula is a conventional representation of a semipolar bond. Examples of suitable phosphine oxides are: dodecyldimethylphosphine oxide, tetradecyldmethylphosphone oxide, tetradecylmethylethylphosphine oxide, 3,6,9-trioxaoctadecyldimethylphosphine oxide, cetyldimethylphosphine oxide, 3-dodecoxy-2-hydroxypropyldi(2-hydroxyethyl) phosphine oxide, stearyldimethylphosphone oxide, cetylethylpropylphosphine oxide, oleyldiethylphosphine oxide, dodecyldiethylphosphine oxide, tetradecyldiethylphosphine oxide, dodecyldipropylphosphine oxide, dodecyldi(hydroxymethyl)phosphine oxide, dodecyldi(2-hydroxyethyl)phosphine oxide, tetradecylmethyl-2-hydroxypropylphosphine oxide, oleyldimethylphosphine oxide, 2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contain alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include: octadecyl methyl sulfoxide, 2-ketotridecyl methyl sulfoxide, 3,6,9-trioxaoctadecyl 2-hydroxyethyl sulfoxide, dodecyl methyl sulfoxide, oleyl 3-hydroxypropyl sulfoxide, tetradecyl methyl sulfoxide, 3-methoxytridecyl methyl sulfoxide, 3-hydroxytridecyl methyl sulfoxide, 3-hydroxy-4-dodecoxybutyl methyl sulfoxide.

Many additional nonsoap surfactants are described in McCUTCHEON'S, DETERGENTS AND EMULSIFIERS, 1986 ANNUAL, published by Allured Publishing Corporation, which is incorporated herein by reference.

The above-mentioned surfactants can be used alone or in combination in the shampoo compositions of the present invention. The anionic surfactants, particularly the alkyl sulfates, the zethoxylated alkyl sulfates and mixtures thereof are preferred for use herein as well as the isethionates.

Selenium Sulfide

Selenium sulfide is a staple item of commerce. Selenium sulfide is generally regarded as a compound having one mole of selenium and two moles of sulfur. However, it may take the form of a cyclic structure, $Se_xS_y$, wherein $x+y=8$.

Selenium sulfide as provided by suppliers can be used in the present compositions provided the particle size of the selenium sulfide particles, on an average, is less than about 25 $\mu$m, preferably less than about 15 $\mu$m. These measurements are made using a forward laser light scattering device (e.g., a Malvern 3600 instrument).

Selenium sulfide is present in the compositions of this invention at a level of from about 0.1% to about 5.0%, preferably from about 0.6% to about 2.5%.

Suspending Systems

Xanthan gum is one of two agents used to suspend the selenium sulfide in the present compositions. This biosynthetic gum material is commercially available and is a heteropolysaccharide with a molecular weight of greater than 1 million. It is believed to contain D-glucose, D-mannose and D-glucuronate in the molar ratio of 2.8:0:2.0. The polysaccharide is partially acetylated with 4.7% acetyl. This information and other is found in Whistler, Roy L. Editor *Industrial Gums—Polysaccharides and Their Derivatives,* New York; Academic Press, 1973. Kelco, a Division of Merck & Co., Inc. offers xanthan gum as Keltrol ®, The suspending agent is present at a level of from about 0.05% to about 1.0%, preferably from about 0.20% to about 0.40% in the present compositions.

The second member of the suspending agent system is a magnesium aluminum silicate having the formula $Al_2Mg_8Si_2$. This material occurs naturally in such smectite minerals as colerainite, saponite and sapphire. Refined magnesium aluminum silicates useful herein are readily available, such as veegum, manufactured by R. T. Vanderbilt Company, Inc. This material is present in the present compositions at a level of from about 0.10% to about 3.00%, preferably from about 0.50% to about 2.00%.

Water

Water is the last essential component of the present invention and forms the remainder of the composition. It is generally present at a level of from about 20% to about 95%, preferably from about 60% to about 85%.

Optional Components

Preferred optional component for use in the present compositions is an amide. The amide used in the present compositions can be any of the alkanolamides of fatty acids known for use in shampoos. These are generally mono- and diethanolamides of fatty acids having from about 8 to about 14 carbon atoms. Preferred are coconut monoethanolamide, lauric diethanolamide and mixtures thereof. The amide is present at a level of from about 1% to about 10%.

Another suitable optional component useful in the present compositions is a nonvolatile silicone fluid. The nonvolatile silicone fluid may be either a polyalkyl siloxane, a polyaryl siloxane, a polyalkylaryl siloxane or a polyether siloxane copolymer and is present at a level of from about 0.1% to about 10.00%, preferably from about 0.5% to about 5.0%. Mixtures of these fluids may also be used and are preferred in certain executions. The dispersed silicone particles should also be insoluble in the shampoo matrix. This is the meaning of "insoluble" as used hereinbefore and hereinafter.

The essentially nonvolatile polyalkyl siloxane fluids that may be used include, for example, polydimethyl siloxanes with viscosities ranging from about 5 to 600,000 centistokes at 25° C. These siloxanes are available, for example, from the General Electric Company as the Viscasil series and from Dow Corning as the Dow Corning 200 series. The viscosity can be measured by means of a glass capillary viscometer as set forth in Dow Corning Corporate Test Method CTM0004, July 20, 1970. Preferably the viscosity range from about 350 centistokes to about 100,000 centistokes.

The essentially nonvolatile polyalkylaryl siloxane fluids that may be used include, for example, polymethylphenylsiloxanes having viscosities of about 15 to 30,000 centistokes at 25° C. These siloxanes are available, for example, from the General Electric Company as SF 1075 methyl phenyl fluoride or from Dow Corning as 556 Cosmetic Grade Fluid.

The essentially nonvolatile polyether siloxane copolymer that may be used is, for example, a polypropylene oxide modified dimethylpolysiloxane (e.g., Dow Corning DC-1248) although ethylene oxide or mixtures of ethylene oxide and propylene oxide may also be used.

Reference disclosing suitable silicone fluids include the previously mentioned U.S. Pat. No. 2,826,551 to Green; U.S. Pat. No. 3,964,500, June 22, 1976 to Drakoff; U.S. Pat. No. 4,364,837 to Pader and British Patent No. 849,433 to Woolston. All of these patents are incorporated herein by reference. Also incorporated herein by reference is Silicon Compounds distributed by Petrarch Systems, Inc., 1984. This reference provides a very good listing of suitable silicone materials.

Another silicone material found especially useful in the present compositions to provide good dry combing is a silicone gum. Silicone gums described by Petrarch and others including U.S. Pat. No. 4,152,416, May 1, 1979 to Spitzer et al. and Noll, Walter, Chemistry and Technology of Silicones, New York: Academic Press 1968. Also describing silicone gums are General Electric Silicone Rubber Product Data Sheets SE 30, SE 33, SE 54 and SE 76. All of these described references are incorporated herein by reference. "Silicone gum" materials denote high molecule weight polydiorganosiloxanes having a mass molecular weight of from about 200,000 to about 1,000,000. Specific examples include polydimethylsiloxane, (polydimethylsiloxane) (methylvinylsiloxane) copolymer, poly(dimethylsiloxane) (diphenyl) (methylvinylsiloxane) copolymer and mixtures thereof.

The shampoos herein can contain a variety of other non-essential optional components suitable for rendering such compositions more acceptable. Such conventional optional ingredients are well known to those skilled in the art, e.g., preservatives such as benzyl alcohol, methyl paraben, propyl paraben and imidazolidinyl urea; cationic surfactants such as cetyl trimethyl ammonium chloride, lauryl trimethyl ammonium chloride, tricetyl methyl ammonium chloride, stearyldimethyl benzyl ammonium chloride, and di(partially hydrogenated tallow) dimethylammonium chloride; menthol; thickeners and viscosity modifiers such as block polymers of ethylene oxide and propylene oxide such as Pluronic F88 offered by BASF Wyandotte, sodium chloride, sodium sulfate, propylene glycol, and ethyl alcohol; pH adjusting agents such as citric acid, succinic acid, phosphoric acid, sodium hydroxide, sodium carbonate, etc.; perfumes; dyes; and, sequestering agents such as disodium ethylenediamine tetraacetate. Such agents generally are used individually at a level of from about 0.01% to about 10%, preferably from about 0.5% to about 5.0% by weight of the composition.

Another desirable optional component is a nonionic polymeric material to keep the selenium sulfide particles dispersed. A preferred material is hydroxypropylmethyl cellulose used at a level of from about 0.001% to about 0.1%, preferably from about 0.002% to about 0.05%.

The pH of the present compositions is generally not critical and may be obtained through the proper selection of surfactants or through the use of appropriate buffer systems to control pH such as citric acid/sodium citrate. Improved color stability is, however, achieved by maintaining the pH within the range of from about 2 to about 6, preferably from about 3 to about 5.

METHOD OF MANUFACTURE

One method for manufacturing the present composition is described below in the Examples.

INDUSTRIAL APPLICABILITY

The present compositions are used in a conventional manner for cleaning hair. From about 0.1 g to about 10 g of a composition is applied to hair that has been wetted, generally with water, worked through the hair and then rinsed out.

The following Examples further describe and demonstrate the preferred embodiments within the scope of the present invention. The Examples are given solely for the purpose of illustration and are not to be construed as limitations of the present invention as many variations thereof are possible without departing from its spirit and scope.

EXAMPLES I-IV

The following are compositions representative of the present invention.

|  | I | II | III | IV |
| --- | --- | --- | --- | --- |
| A - Main Mix | | | | |
| Double reverse osmosis (DRO) Water | 1.16 | 6.16 | — | 2.74 |
| Ammonium Laureth Sulfate (28%) | 40.48 | 40.48 | 5.30 | 5.30 |
| Ammonium Lauryl Sulfate (25%) | 12.9 | 12.9 | 51.20 | 54.00 |
| Ammonium Xylene Sulfonate (41.5%) | 5.0 | 5.0 | 5.00 | 4.00 |
| Xanthan Gum | 0.3 | 0.3 | 0.30 | 0.30 |
| Cocamide MEA (85%) | 3.0 | 3.0 | 1.50 | 1.50 |
| Citric Acid (50%) | 0.59 | 0.59 | 0.59 | 0.59 |
| Sodium Citrate (38%) | 0.71 | 0.71 | 0.71 | 0.71 |
| Cetyl Alcohol | 0.42 | 0.42 | 0.42 | 0.42 |
| Stearyl Alcohol | 0.17 | 0.17 | 0.17 | 0.17 |
| Tricetylmethyl Ammonium Chloride (87%) | 0.57 | 0.57 | 0.57 | 0.57 |
| Perfume | 0.65 | 0.65 | 0.65 | 0.65 |
| Preservative (1.5%) | 0.03 | 0.03 | 0.03 | 0.03 |
| B - Silicone Mix | | | | |
| Ammonium Laureth Sulfate (28%) | 8.99 | 8.99 | 8.99 | 8.99 |
| Stearyl Alcohol | 0.01 | 0.01 | 0.01 | 0.01 |
| Cetyl Alcohol | — | — | — | — |
| Dimethicone | 1.0 | 1.0 | 1.0 | 1.0 |
| C - Magnesium Aluminum Silicate Mix | | | | |
| Magnesium Aluminum Silicate | 1.0 | 0.75 | 1.0 | 0.75 |
| DRO Water | 19.0 | 14.25 | 18.54 | 14.25 |
| D - Selenium Disulfide Mix | | | | |
| Selenium Disulfide | 1.0 | 1.0 | 1.0 | 1.0 |
| Hydroxypropyl methylcellulose | 0.02 | 0.02 | 0.02 | 0.02 |
| Sodium Alkyl Sulfate (25%) | 0.16 | 0.16 | 0.16 | 0.16 |
| Preservative | 0.02 | 0.02 | 0.02 | 0.02 |
| Sodium Citrate | 0.04 | 0.04 | 0.04 | 0.04 |
| Citric Acid | 0.03 | 0.03 | 0.03 | 0.03 |
| DRO Water | 2.75 | 2.75 | 2.75 | 2.75 |
| | 100.00 | 100.00 | 100.00 | 100.00 |

All dilutions referred to in the formulae are in water.

The above compositions are prepared by heating mixes A, B and C separately to a temperature of from about 71° C. to about 82° C. These separate mixes are then mixed together at a temperature of about 38° C. The selenium sulfide mix, D, is then added and the entire mixture is mixed thoroughly.

What is claimed is:

1. A lotion shampoo composition comprising:
   (a) from about 10% to about 30% of a synthetic surfactant selected from the group consisting of anionic surfactant, zwitherionic surfactants, amphoteric surfactants and mixtures thereof;
   (b) from about 0.1% to about 5.0% of selenium sulfide having an average particle size of less than about 25 μm;
   (c) from about 0.02% to about 0.40% of a xanthan gum;
   (d) from about 0.5% to about 2.0% of a magnesium aluminum silicate; and
   (e) the remainder water.

2. A shampoo composition according to claim 1 wherein the surfactant is anionic.

3. A shampoo composition according to claim 2 wherein the anionic surfactant is selected from the group consisting of alkyl sulfate, ethoxylated alkyl sulfates and mixtures thereof.

4. A shampoo composition according to claim 2 which in addition contains a nonvolatile silicone at a level of from about 0.1% to about 10%.

5. A shampoo compositions according to claim 3 which in addition contains an amide at a level of from about 1% to about 10%.

6. A shampoo composition according to claim 4 wherein the nonvolatile silicone is a mixture of silicone fluids and silicone gums.

7. A method of shampooing hair comprising applying to hair that has been wet with water from about 0.10 g to about 10 g of a composition according to claim 1, working the composition through the hair and rinsing it from the hair.

* * * * *

UNITED STATES PATENT AND TRADEMARK OFFICE
CERTIFICATE OF CORRECTION

PATENT NO. : 4,927,563

DATED : May 22, 1990

INVENTOR(S) : Patrick C. McCall

It is certified that error appears in the above-identified patent and that said Letters Patent is hereby corrected as shown below:

Column 1, line 34, "1,051,258" should read -- 1,051,268 --.

Column 4, line 53, "R∆" should read -- R" --.

Column 5, line 50, "2.8:0:2.0" should read -- 2.8:2.0:2.0 --.

Column 6, line 52, "Green" should read -- Geen --.

Column 8, line 55, "claim 2" should read -- claim 3 --.

Column 8, line 58, "claim 3" should read -- claim 4 --.

Column 8, line 61, "claim 4" should read -- claim 5 --.

Signed and Sealed this

Twenty-second Day of September, 1992

Attest:

DOUGLAS B. COMER

*Attesting Officer*   *Acting Commissioner of Patents and Trademarks*